US00PP36319P3

(12) United States Plant Patent
Vinson

(10) Patent No.: US PP36,319 P3
(45) Date of Patent: Dec. 17, 2024

(54) ***VACCINIUM* PLANT NAMED 'BWPBLUE02'**

(50) Latin Name: *Vaccinium corymbosum*
Varietal Denomination: BWPBLUE02

(71) Applicant: BerryWorld Plus Ltd, Oxfordshire (GB)

(72) Inventor: Peter Edward Vinson, Faversham (GB)

(73) Assignees: BERRY WORLD PLUS LTD., Oxfordshire (GB); NORTH CAROLINA STATE UNIVERSITY OFFICE OF RESEARCH, Raleigh, NC (US)

( * ) Notice: Subject to any disclaimer, the term of this patent is extended or adjusted under 35 U.S.C. 154(b) by 0 days.

(21) Appl. No.: 18/528,221

(22) Filed: Dec. 4, 2023

(65) Prior Publication Data

US 2024/0251690 P1 Jul. 25, 2024

(30) Foreign Application Priority Data

Jan. 23, 2023 (QZ) ..... PBR 20230231

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ... A01H 5/08; A01H 5/02; A01H 5/00; A01H 6/368; A01H 6/36
See application file for complete search history.

(56) References Cited

U.S. PATENT DOCUMENTS

PP15,103 P3 * 8/2004 Hancock ..... A01H 6/368 Plt./157
PP24,697 P3 * 7/2014 Brazelton ..... A01H 5/08 Plt./157

* cited by examiner

*Primary Examiner* — June Hwu
(74) *Attorney, Agent, or Firm* — Penny J. Aguirre

(57) ABSTRACT

A new cultivar of *Vaccinium* plant named 'BWPBLUE02' that is characterized by its mid-season fruit ripening, its upright, easy to manage plant habit, its concentrated harvest window, its fruit that are brilliant purplish-blue in color, its fruit with a good balance of sugar and acid, its fruit with small, shallow flower calyx scar and picking scar, and its fruit with excellent post-harvest shelf life.

2 Drawing Sheets

Botanical classification: *Vaccinium corymbosum.*
Cultivar designation: 'BWPBLUE02'.

CROSS REFERENCE TO RELATED APPLICATIONS

This application claims priority to European Community Plant Variety Office (CPVO) Plant Breeder's Rights Application No. 2023/0231 filed on Jan. 23, 2023, under 35 U.S.C. 119(f), the entire contents of which is incorporated by reference herein. This Application is also related to United Kingdom International Plant Protection Convention (IPPC) Application No. 23/826 filed Apr. 28, 2023. The Applicant received the information for the Plant breeders' rights applications directly from the Inventor.

BACKGROUND OF THE INVENTION

The present invention relates to a new and distinct cultivar of *Vaccinium corymbosum* and will be referred to hereafter by its cultivar name, 'BWPBLUE02'. 'BWPBLUE02' is a new cultivar of Northern highbush blueberry grown for fruit production.

The new cultivar was derived from a controlled breeding program by the Inventor in Faversham, Kent, The United Kingdom. The goal of the breeding program is to develop new cultivars of *Vaccinium corymbosum* with early fruit set and fruit with desirable quality, size, and yield. The Inventor made a cross in 2010 between 'NC4122' (unpatented) as the female parent and 'Duke' (unpatented) as the male parent. 'BWPBLUE02' was selected as a single unique plant in 2014 from amongst the resulting seedlings.

Asexual propagation of the new cultivar was first accomplished under the direction of the Inventor by semi-hardwood cuttings in Faversham, Kent, The United Kingdom in 2015. Asexual propagation by semi-hardwood cuttings and tissue culture using meristematic tissue has determined that the characteristics of this cultivar are stable and are reproduced true to type in successive generations.

SUMMARY OF THE INVENTION

The following traits have been repeatedly observed and represent the characteristics of the new cultivar, which in combination distinguish 'BWPBLUE02' as a new and distinct cultivar of *Vaccinium.*

1. 'BWPBLUE02' exhibits mid-season fruit ripening.
2. 'BWPBLUE02' exhibits an upright, easy to manage plant habit.
3. 'BWPBLUE02' exhibits a concentrated harvest window.

4. 'BWPBLUE02' exhibits fruit that are brilliant purplish-blue in color.
5. 'BWPBLUE02' exhibits fruit with a good balance of sugar and acid.
6. 'BWPBLUE02' exhibits fruit with small, shallow flower calx scar and picking scar.
7. 'BWPBLUE02' exhibits fruit with excellent post-harvest shelf life.

The female parent plant of 'BWPBLUE02' differs from 'BWPBLUE02' in having a less vigorous plant habit, a lower chill requirement, and fruit with a much lower yield, an earlier ripening season, and smaller and less firm with less flavor. The male parent plant of 'BWPBLUE02' differs from 'BWPBLUE02' in having a less vigorous plant habit, an earlier flowering season, and fruit with an earlier harvest season that are smaller and less firm with less flavor. 'BWPBLUE02' can also be compared to the *Vaccinium* cultivars 'Draper' (U.S. Plant Pat. No. 15,103 P2) and 'Topshelf' (U.S. Plant Pat. No. 24,697). 'Draper' is similar to 'BWPBLUE02' in blooming and harvesting seasons and fruit size. 'Draper' differs from 'BWPBLUE02' in having a less upright plant habit and fruit that are less flavorful, less firm, and have a lower chill requirement. 'Topshelf' is similar to 'BWPBLUE02' in having an upright plant habit and blooming and producing firm fruit in early-mid season. 'Topshelf' differs from 'BWPBLUE02' in having smaller sized fruit and a lower fruit yield.

BRIEF DESCRIPTION OF THE DRAWINGS

The accompanying color photographs illustrate the overall appearance and distinct characteristics of the new *Vaccinium*. The photographs were taken of 7-year-old plants of the new cultivar as grown in outdoors in 15-liter pots in Faversham, Kent, United Kingdom.

The photograph in FIG. 1 provides a side view of 'BWPBLUE02' in spring after fully leafing out.

Figure 1:
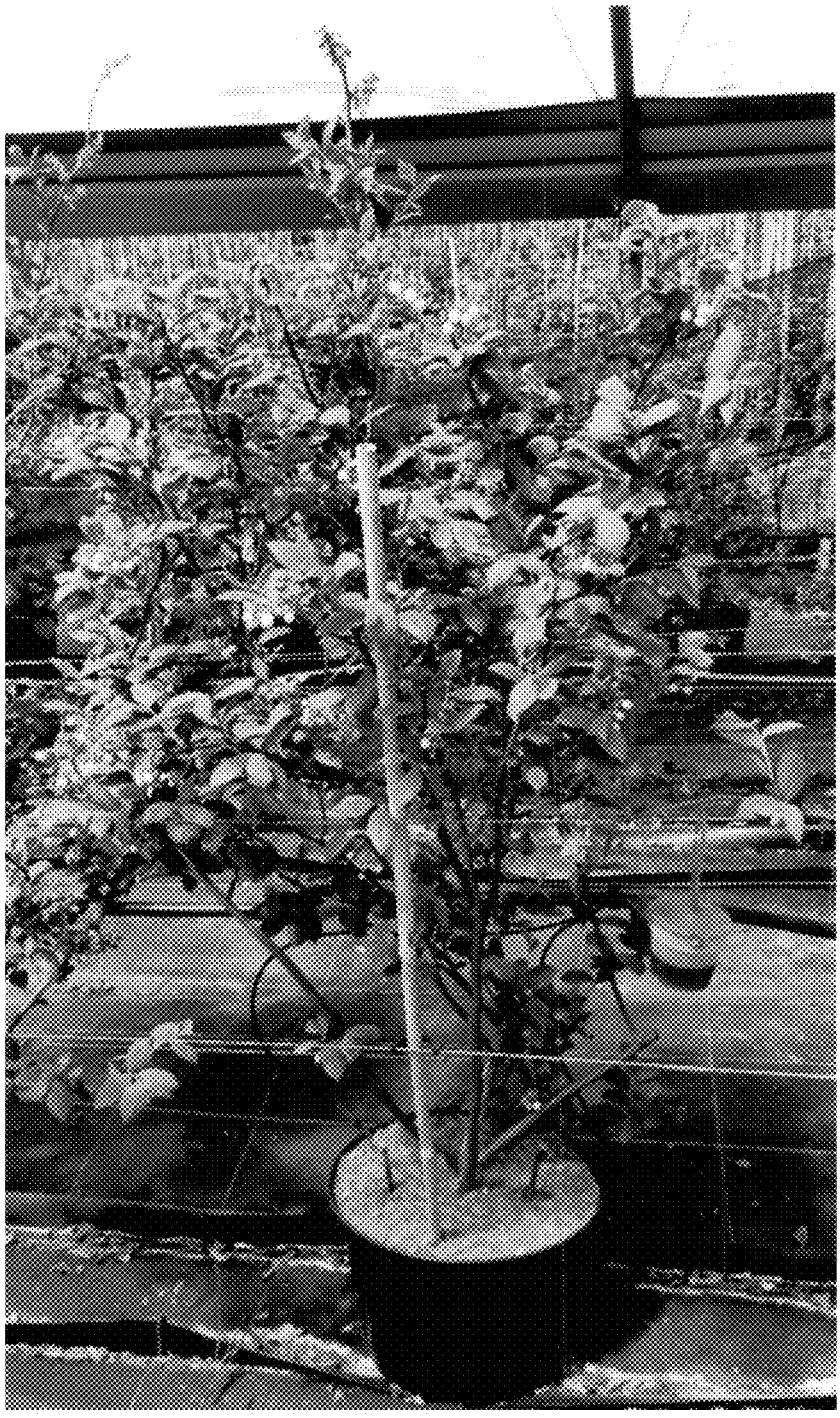
Figure 2:
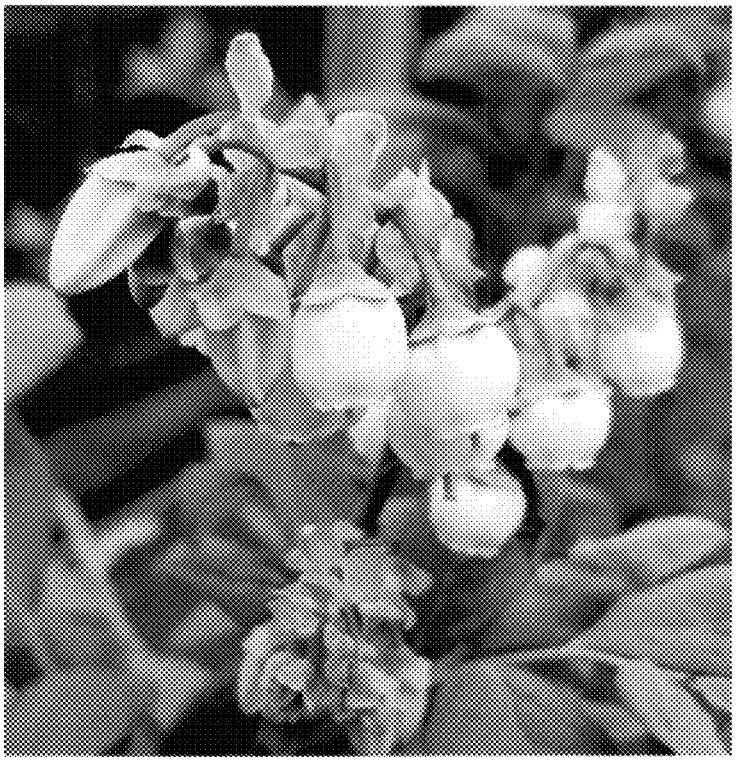

The photograph in FIG. 2 provides a view of the mature flowers of 'BWPBLUE02'.

Figure 3:
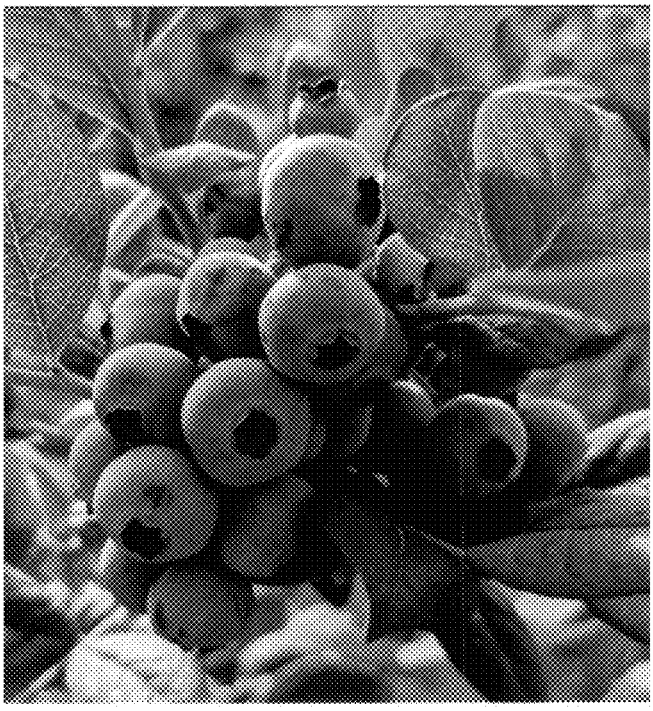

The photograph in FIG. 3 provides a close-up view of the mature fruit of 'BWPBLUE02'.

The colors in the photographs are as close as possible with the digital photography and printing techniques utilized and the color codes in the detailed botanical description accurately describe the new *Vaccinium*.

DETAILED BOTANICAL DESCRIPTION OF THE PLANT

The following is a detailed description of 7-year-old plants of the new cultivar as grown outdoors in 15-liter containers in Faversham, Kent, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General plant characteristics:

*Plant type.*—Deciduous, fruit-producing shrub.

*Fruiting type.*—On one-year-old canes only.

*Plant habit.*—Upright.

*Height and spread.*—Average of 1.42 m in height and 1.13 cm in width as a 7-year-old plant as grown in a container.

*Cold hardiness.*—Frost tolerant in bud and flower, fruit has not been tested under 3° C.

*Disease and pest resistance.*—No susceptibility or resistance to diseases or pests has been observed.

*Root description.*—Fibrous, some roots thicker and anchored.

*Growth rate.*—Fast and vigorous.

*Propagation.*—Semi-hardwood cuttings and tissue culture.

*Root development.*—A tissue culture plantlet will root in a 15-cc plug in about 8 weeks with an additional 6 weeks to fully root in 350-cc liner, a cutting will initiate roots in 4 to 8 weeks and fully roots in a 70-cc plug in 12 to 16 weeks.

*Chill requirement.*—Approximated 1000 hours below 7° C.

Stem description:

*Canes per plant.*—Average of 5, following biannual, commercial style pruning in February (winter) and June (summer).

*Stem color.*—Current year's growth; 144A, flushed with 61A, dormant stems (previous year's growth); 177B, with striations of 177C and 144A.

*Branching.*—Moderately branched, an average of 5 main branches and 4 to 7 lateral branches per stem, initial branch occurs about 22 cm from base and subsequent branches occur an average of 4.41 cm apart.

*Stem surface.*—Rough texture.

*Stem aspect.*—Main branch; vertical, lateral branches; average of 45° to the main branch.

*Stem size.*—An average of 1.28 m in length and 2.15 cm in diameter.

*Stem strength.*—High.

*Internodes.*—5 to 6 cm in length.

*Twiginess.*—Low.

Foliage description:

*Leaf shape.*—Elliptic.

*Leaf division.*—Simple.

*Leaf base.*—Aequilateral.

*Leaf apex.*—Acute.

*Leaf venation.*—Pinnipalmate, reticulate network occasionally suffused midway from petiole with other veins, color on upper and lower surface 144C.

*Leaf margins.*—Entire.

*Leaf attachment.*—Petiolate.

*Leaf arrangement.*—Alternate.

*Leaf orientation.*—Semi-upright to horizontal.

*Leaf surface.*—Both surfaces glabrous, slightly waxy.

*Leaf color.*—Upper surface (spring, summer); 144A, mottled towards the margins with 61A, lower surface (spring, summer); 147B, flushed at the margins with 61A, upper surface (fall); a blend of 144A, N144A, 60A, 59A, and N170B, lower surface (fall); a blend of 147B, 139D, 59D, 25D, and 15D.

*Leaf size.*—Average of 4.7 cm in length, 2.3 cm in width.

*Leaf blade length.*—Width ratio. — 2:1.

*Synchrony of leafing and flowering.*—Flowers are produced first, followed by leaves.

*Time of beginning of vegetative growth.*—Medium, May in Faversham, Kent, United Kingdom.

*Petioles.*—Round in shape, an average of 4.5 mm in length and 2 mm in width, surfaces are glabrous, color; upper surface N144D, lower surface 60C.

*Stipules.*—None observed.

*Leaf nectaries.*—Some observed, minute.

Inflorescence description:

*Bloom season.*—Early, starts in April, 50% in bloom late April, blooms through May in Faversham, Kent, United Kingdom.

*Inflorescence type.*—Panicle.

*Inflorescence size.*—Average of 6.6 cm in length and 3.7 cm in width.

*Lastingness of inflorescence.*—30 to 40 days but highly dependent on air temperatures.

*Number of flowers.*—Average of 8 per inflorescence, range of 6 to 9.

*Flower fragrance.*—Light floral fragrance.

*Flower size.*—Average of 1.2 cm in length and 9 mm in width.

*Flower buds.*—8 per inflorescence, oval in shape, 1.1 cm in length and 5.2 mm in width, strongly ridged surface at petal margins, color immature; 14D and slightly flushed with 63A, mature before burst 157A.

*Corolla.*—Urceolate in shape, comprised of 5 fused petals with tip free and curled under, ridges when mature medium, average of 9 mm in length and 9 mm in width, aperture is an average of 5.5 mm in diameter, self-cleaning, both surfaces glabrous, 155C in color, protrusion of stigma is definite, average of 1.9 mm beyond the edge of the corolla.

*Calyx.*—Campanulate, comprised of 5 to 6 fused sepals with lobes free at apex, average of 2.7 mm in length, 8 mm in width at anthesis, surface is glabrous, color; upper side 143B, lower side 143D.

*Pedicels.*—Round, average of 8.4 mm in length and 0.9 mm in width, surface is glabrous, color; upper side 63A, lower side 143C.

*Peduncles.*—Round, an average of 2.3 mm in length and 2 mm in width, surface is glabrous, color; upper side 63A, lower side 143C.

Reproductive organs:

*Androecium.*—Stamens; 9, filament; 3.4 mm in length, 0.8 mm in width, N144D in color, anthers; average of 4.4 mm in length, 0.6 mm in width, N167A, dorsifixed in shape, pollen; high in quantity, 163D in color.

*Gynoecium.*—Pistil; 1, 1.2 cm in length, style; 8.9 mm in length, stigma; 0.6 mm in diameter, ovary; inferior, 143B in color, 3 mm in length, 1.4 mm in width.

Fruit description:

*Type.*—Berry.

*Fruit development.*—Average of 88 days.

*Infructescence density.*—Medium. Time of 50% maturity. — June in Faversham, Kent, United Kingdom.

*Number.*—Average of 1,991 berries per plant.

*Fruit bearing season.*—Mid-season, early July to August in in Faversham, Kent, United Kingdom.

*Fruit size.*—Large, average of 2.2 cm in diameter, 1.5 cm in height.

*Fruit shape.*—Oblate.

*Fruit sepal attitude.*—Straight.

*Fruit weight.*—Average of 4.44 g per berry.

*Fruit firmness.*—Firm, average of 90.9 Shore O.

*Fruit stem scar.*—Small, shallow and dry, average of 1.8 mm in diameter.

*Fruit calyx* (*flower scar*).—Average of 8 mm in diameter, 2 mm in depth.

*Fruit taste.*—Good balance of sugar and acid.

*Brix.*—12.7°.

*Acid.*—0.78 g/L.

*Fruit texture.*—Firm, juicy.

*Fruit ripening.*—Average of 59 days.

*Fruit storage.*—Excellent, 6 to 7 weeks with little decay or loss of fruit quality.

*Fruit productivity* (*yield*).—High, 6.2 kg per bush on 6-year-old plants (recorded in site trials in Faversham, UK in 2022).

*Persistence of calyx.*—Not persistent.

*Surface.*—Glossy, smooth, glabrous with wax (bloom) removed.

*Abundance and persistence of wax.*—Medium abundance, persistent.

*Skin color.*—Immature fruit; with wax 142D, with wax removed N144C, mature fruit; with wax 97A, with wax removed 203C.

*Flesh color.*—144D.

*Fruit shape.*—Oblate.

*Fruit use.*—Fresh produce.

Seed description:

*Seed shape.*—Oblong to oval.

*Seed quantity.*—Abundant, 50 per fruit.

*Seed size.*—Average of 1.3 mm in length, 0.8 mm in width.

*Seed color.*—164B.

*Seed surface.*—Glabrous.

*Seed weight.*—0.005 g/10 seeds.

It is claimed:

1. A new and distinct cultivar of *Vaccinium* plant named 'BWPBLUE02' as herein illustrated and described.

* * * * *